United States Patent
Sashida et al.

Patent Number: 5,648,451
Date of Patent: Jul. 15, 1997

[54] PROCESS FOR PRODUCING PHOTOSENSITIVE RESIN

[75] Inventors: Nobuyuki Sashida; Toshio Banba; Naoshige Takeda, all of Utsunomiya, Japan

[73] Assignee: Sumitomo Bakelite Company Limited, Tokyo, Japan

[21] Appl. No.: 541,582

[22] Filed: Oct. 10, 1995

[51] Int. Cl.$^6$ .......................... C08G 69/26; C08G 73/10
[52] U.S. Cl. .......... 528/353; 528/125; 528/128; 528/170; 528/172; 528/173; 528/179; 528/183; 528/185; 528/220; 528/229; 528/350; 525/420; 525/436
[58] Field of Search .................. 528/125, 128, 528/353, 170, 179, 172, 173, 183, 185, 220, 229, 350; 525/420, 436

[56] References Cited

U.S. PATENT DOCUMENTS

| | | | |
|---|---|---|---|
| 3,957,512 | 5/1976 | Kleeberg et al. | 96/35.1 |
| 4,040,831 | 8/1977 | Rubner et al. | 96/35.1 |
| 4,598,038 | 7/1986 | Ahne | 430/283 |
| 5,262,277 | 11/1993 | Sato et al. | 430/283 |
| 5,348,835 | 9/1994 | Oba et al. | 528/353 |
| 5,518,864 | 5/1996 | Oba et al. | 430/330 |

OTHER PUBLICATIONS

"Preparation & Properties of Photosensitive Polyimides Using 1–Hydroxy benzotoriazole as a condensing agent", T. Banba pp. 93–94, International Symposium on Advanced Network–Polymers, Dec. 5–6, 1995.

*Primary Examiner*—James J. Seidleck
*Assistant Examiner*—P. Hampton-Hightower
*Attorney, Agent, or Firm*—Browdy and Neimark

[57] ABSTRACT

A process for producing a photosensitive resin, comprises reacting a diamine with a tetracarboxylic acid tetraester represented by the formula (1) at a temperature of 0° to 50° C. in an aprotic polar solvent:

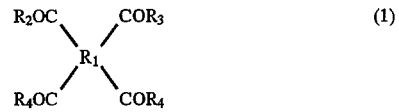

(1)

wherein $R_1$ is a tetravalent organic group; $R_2$ is a group represented by the formula:

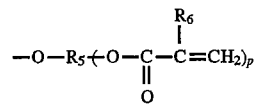

in which $R_5$ is a divalent to hexavalent organic group, $R_6$ is H or $CH_3$ and p is an integer of 1 to 5; $R_3$ is a group represented by $-OCH_3$, $-OC_2H_5$, $-OC_3H_7$ or the formula:

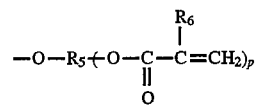

and $R_4$ is a group of the formula:

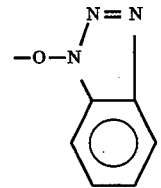

the tetracarboxylic acid tetraester of the formula (1) is obtained by subjecting to addition reaction a tetracarboxylic dianhydride, an alcohol compound represented by the formula $R_2H$ in which $R_2$ is as defined above and an alcohol compound represented by the formula $R_3H$ in which $R_3$ is as defined above and thereafter subjecting the resulting addition reaction product to dehydration-condensation with 1-hydroxy-1,2,3-benzotriazole using a carbodiimide compound as a condensation agent.

8 Claims, No Drawings

PROCESS FOR PRODUCING PHOTOSENSITIVE RESIN

BACKGROUND OF THE INVENTION

1. Field of the Invention

This invention relates to a process for producing a photosensitive resin having a high molecular weight.

2. Related Art Statement

A polyimide having excellent heat resistance, and prominent electrical insulation properties, mechanical strength and the like has heretofore been used as a surface-protective film of a semiconductor device, an interlaminar insulating film of a semiconductor device or the like. However, in order to simplify the complicated process for preparing a polyimide pattern, attention has recently been paid to a technique for photosensitizing the polyimide per se. For example, a polyimide precursor composition which has been photosensitized by an ester group having a structure represented by the following formula or the like is known (see, for example, U.S. Pat. No. 4,040,831):

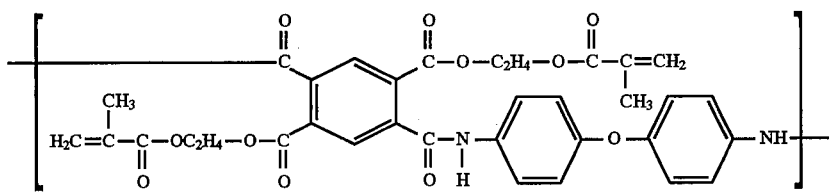

In all of the above cases, the photosensitized polyimide precursor composition is dissolved in a suitable organic solvent, the resulting varnish is coated on a substrate and the resulting assembly is dried, irradiated with an ultraviolet ray through a photomask, developed and then rinsed to form the desired pattern, after which the assembly having the desired pattern is further heat-treated to obtain a polyimide film.

When the photosensitized polyimide is used, in addition to such an effect that the pattern-forming step is simplified, the process is safe and low in environmental pollution because it is not necessary to use an etching solution having a strong toxicity. Therefore, the photosensitization of polyimide is expected to become a more important technique in the future.

As a process for introducing an ester group into a polyimide, there is reported a process which comprises first reacting an acid dianhydride with an alcohol compound having a photosensitive group, then converting the reaction product to an acid chloride and thereafter copolymerizing the resulting acid chloride with a diamine (see U.S. Pat. No. 4,040,831). Also, a process in which a carbodiimide is used as a condensation agent in the above condensation reaction is known (see U.S. Pat. No. 4,654,415 and Japanese Patent Application Kokai (Laid-Open) No. 61-293,204). The resin synthesized using the carbodiimide has such a benefit that the chlorine content is as small as less than several ppm, but has the following problems.

In general, carbodiimides are condensation agents which are used in the synthesis of a peptide from an amino acid. The reaction mechanism is such that the carbodiimide is first reacted with a carboxylic acid to produce an O-acylisourea, this O-acylisourea is further reacted with another molecule having carboxyl group to form a symmetric acid anhydride, and this anhydride is reacted with an amine to form an amido linkage. However, in this reaction, if a strong basic amine is present in the reaction system, the O-acylisourea is rearranged as a side reaction to produce an acylurea having no reactivity as a by-product.

When it is intended to obtain a photosensitive resin, a polyimide precursor is produced using a carbodiimide from a diamine and a tetracarboxylic acid diester having an acryl or methacryl group obtained by a reaction between an alcohol compound having a photosensitive group and an acid dianhydride; however, unlike the case where a polyamide is obtained from a usual dicarboxylic acid and a diamine, the tetracarboxylic diester having an acryl or methacryl group which is very great in steric hindrance hardly forms a symmetric anhydride and is very low in reactivity.

Also, for the above-mentioned reason, an acylurea is formed as a by-product to terminate the end of the product and hence the formation of a high molecular weight compound becomes very difficult. Therefore, in order to inhibit the side reaction, the reaction is effected at a low temperature in some methods. However, in this case, it is difficult to completely inhibit the side reaction because of heat generation due to reaction or the like and only a polyimide precursor having a low molecular weight is obtained. Also, the reaction method has been extensively studied. For example, the Journal of Chemical Society of Japan, Vol. 80, No. 12 (1959) shows on page 1497 an example in which N,N'-dicyclohexylcarbodiimide (referred to hereinafter as DCC) is used as the carbodiimide, and reports that when the acid and the DCC are allowed to react for a while and thereafter the amine is gradually added dropwise, the production of N-acylurea can be more sufficiently inhibited than when the necessary amounts of the acid, the amine and the DCC are added at one time at the beginning.

However, even if the polyimide precursor is synthesized taking the addition order into consideration (see Japanese Patent Application Kokai (Laid-Open) No. 61-293,204), actually, only a polyimide precursor having a low molecular weight is obtained. A photosensitive resin composition in which such a low molecular weight polyimide precursor is used has a low sensitivity, and a polyimide film obtained by heat-treating the same is inferior in mechanical characteristics, and hence, there is a problem in its practical use.

3. Object of the Invention

An object of this invention is to provide a process for producing a photosensitive resin having a high molecular weight, as a result of which a photosensitive resin having a high sensitivity and excellent cured film characteristics is obtained.

Other objects and advantages of this invention will become apparent from the following description.

SUMMARY OF THE INVENTION

According to this invention, there is provided a process for producing a photosensitive resin which comprises reacting a diamine with a tetracarboxylic acid tetraester represented by the formula (1):

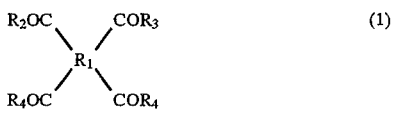

wherein $R_1$ is a tetravalent organic group; $R_2$ is a group represented by the formula:

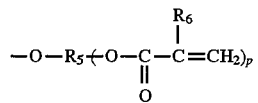

in which $R_5$ is a divalent to hexavalent organic group, $R_6$ is H or $CH_3$ and p is an integer of 1 to 5; $R_3$ is a group represented by $-OCH_3$, $-OC_2H_5$, $-OC_3H_7$ or the formula:

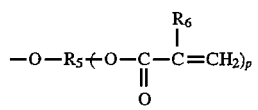

in which $R_5$, $R_6$ and p are as defined above; and $R_4$ is a group of the formula:

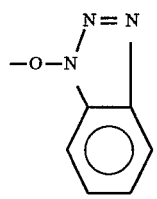

at a temperature of 0° to 50° C. in an aprotic polar solvent. In particular, in the above process, it is preferable to obtain the tetracarboxylic acid tetraester represented by the formula (1) by subjecting to addition reaction a tetracarboxylic dianhydride, an alcohol compound of $R_2H$ and an alcohol compound of $R_3H$ and then subjecting the resulting addition reaction product to dehydration-condensation with 1-hydroxy-1,2,3-benzotriazole using the carbodiimide compound as a condensation agent.

DETAILED DESCRIPTION OF THE INVENTION

The tetracarboxylic acid tetraester of the formula (1) used in this invention can be quantitatively reacted with a diamine to easily produce a polyamic acid ester having a very high molecular weight.

The tetracarboxylic acid tetraester is synthesized by subjecting to addition reaction a tetracarboxylic dianhydride, an alcohol compound of $R_2H$ and an alcohol compound of $R_3H$, and then subjecting the resulting addition reaction product to dehydration-condensation with 1-hydroxy-1,2,3-benzotriazole in the presence of a carbodiimide compound as a condensation agent.

As the tetracarboxylic dianhydride used in this invention, there are mainly used aromatic tetracarboxylic dianhydrides and/or their derivatives. The aromatic tetracarboxylic dianhydride or its derivative includes, for example, pyromellitic dianhydride, benzene-1,2,3,4-tetracarboxylic dianhydride, 3,3',4,4'-benzophenonetetracarboxylic dianhydride, 2,2',3, 3'-benzophenonetetracarboxylic dianhydride, 2,3,3',4'-benzophenonetetracarboxylic dianhydride, naphthalene-2,3,6,7-tetracarboxylic dianhydride, naphthalene-1,2,5,6-tetracarboxylic dianhydride, naphthalene-1,2,4,5-tetracarboxylic dianhydride, naphthalene-1,4,5,8-tetracarboxylic dianhydride, naphthalene-1,2,6,7-tetracarboxylic dianhydride, 4,8-dimethyl-1,2,3,5,6,7-hexahydronaphthalene-1,2,5,6-tetracarboxylic dianhydride, 4,8-dimethyl-1,2,3,5,6,7-hexahydronaphthalene-2,3,6,7-tetracarboxylic dianhydride, 2,6-dichloronaphthalene-1,4,5, 8-tetracarboxylic dianhydride, 2,7-dichloronaphthalene-1,4, 5,8-tetracarboxylic dianhydride, 2,3,6,7-tetrachloronaphthalene-1,4,5,8-tetracarboxylic dianhydride, 1,4,5,8-tetrachloronaphthalene-2,3,6,7-tetracarboxylic dianhydride, 3,3',4,4'-diphenyltetracarboxylic dianhydride, 2,2',3,3'-diphenyltetracarboxylic dianhydride, 2,3,3',4'-diphenyltetracarboxylic dianhydride, 3,3",4,4"-p-terphenyltetracarboxylic dianhydride, 2,2",3,3"-p-terphenyltetracarboxylic dianhydride, 2,3,3",4"-p-terphenyltetracarboxylic dianhydride, 2,2-bis(2,3-dicarboxyphenyl)propane dianhydride, 2,2-bis(3,4-dicarboxyphenyl)propane dianhydride, bis(2,3-dicarboxyphenyl)ether dianhydride, bis(3,4-dicarboxyphenyl)ether dianhydride, bis(2,3-dicarboxyphenyl)methane dianhydride, bis(3,4-dicarboxyphenyl)methane dianhydride, bis(2,3-dicarboxyphenyl)sulfone dianhydride, bis(3,4-dicarboxyphenyl)sulfone dianhydride, 1,1-bis(2,3-dicarboxyphenyl)ethane dianhydride, 1,1-bis(3,4-dicarboxyphenyl)ethane dianhydride, perylene-2,3,8,9-tetracarboxylic dianhydride, perylene-3,4,9,10-tetracarboxylic dianhydride, perylene-4,5,10,11-tetracarboxylic dianhydride, perylene-5,6,11,12-tetracarboxylic dianhydride, phenanthrene-1,2,7,8-tetracarboxylic dianhydride, phenanthrene-1,2,6,7-tetracarboxylic dianhydride, phenanthrene-1,2,9,10-tetracarboxylic dianhydride, cyclopentane-1,2,3,4-tetracarboxylic dianhydride, pyrazine-2,3,5,6-tetracarboxylic dianhydride, pyrrolidine-2,3,4,5-tetracarboxylic dianhydride, thiophene-2,3,4,5-tetracarboxylic dianhydride and the like. However, the aromatic tetracarboxylic dianhydrides and/or their derivatives are not limited to the above-mentioned examples. These aromatic tetracarboxylic dianhydrides and/or their derivatives may be used alone or in admixture of two or more.

The alcohol compounds $R_2H$ and $R_3H$ each having at least one acryl or methacryl group used in this invention are bonded to the polyamide side chain through an ester linkage and the acryl or methacryl groups undergo photocrosslinking reaction, whereby the starting material of a negative type photosensitive resin is obtained. In the alcohol compounds each having at least one acryl or methacryl group, the number of acryl or methacryl groups [p in the formula (1)] is 1 to 5. The alcohol compounds having one or two acryl or methacryl groups are preferred in the points of availability and preservability. When p is zero, photo-crosslinking reaction does not proceed because the alcohol compounds have no acryl or methacryl group. Also, when the alcohol compounds have more than 6 acryl or methacryl groups, said alcohol compounds are difficult to produce in industry and the reaction hardly proceeds.

The alcohol compounds $R_2H$ and $R_3H$ each having at least one acryl or methacryl group include, for example, pentaerythritol triacrylate, pentaerythritol trimethacrylate, pentaerythritol acrylate dimethacrylate, pentaerythritol diacrylate methacrylate, dipentaerythritol pentacrylate, dipentaerythritol pentamethacrylate, glycerol diacrylate, glycerol dimthacrylate, glycerol acrylate methacrylate, 1,3-diacryloylethyl-5-hydroxyethyl isocyanurate, 1,3-dimethacrylate-5-hydroxyethyl isocyanurate, ethylene glycol-modified pentaerythritol triacrylate, propylene glycol-modified pentaerythritol triacrylate, trimethylolpropane diacrylate, trimethylolpropane dimethacrylate, 2-hydroxyethyl methacrylate, 2-hydroxyethyl acrylate, glycidyl methacrylate, glycidyl acrylate, 2-hydroxypropyl methacrylate, 2-hydroxypropyl acrylate, polyethylene glycol-modified methacrylate, polyethylene glycol-modified acrylate, polypropylene glycol-modified acrylate, polypropylene glycol-modified methacrylate and the like. However, the alcohol compounds are not limited to these specific examples. These alcohol compounds may be used alone or in admixture of two or more. In this invention, when $R_3$ is methoxy, ethoxy or propoxy in the tetraester, $R_3$ is derived from methanol, ethanol or propanol, respectively. These esters are used to adjust the sensitivity and solubility. In the synthesis process, a diester of $R_3$ is produced as a by-product in some cases; however, there is no problem.

The carbodiimide compound used in this invention includes dicyclohexylcarbodiimide, ethylcyclohexylcarbodiimide, diethylcarbodiimide, diphenylcarbodiimide, diisopropylcarbodiimide and the like.

1-Hydroxy-1,2,3-benzotriazole can give an active ester compound, because in spite of the fact that the hydroxyl group thereof has a high acidity, the N atom in the β-position to the hydroxyl group stabilizes the ester linkage formed by reaction between the hydroxyl group and a carboxylic acid. Moreover, this stable active ester compound is such a unique compound that when it reacts with a diamine, an amido linkage is easily and quantitatively formed.

This invention is based on the finding that when a dicarboxylic acid diester having at least one acryl or methacryl group in the side chain and having a large steric hindrance is used, a high molecular weight compound is easily obtained as compared with conventional methods.

In the process of this invention, the tetracarboxylic acid tetraester of the formula (1) is reacted with a diamine at a temperature of 0° to 50° C. in an aprotic polar solvent.

The diamine used in this invention is preferably an aromatic diamine and/or its derivative. The diamine includes, for example, m-phenylenediamine, 1-isopropyl-2,4-phenylenediamine, p-phenylenediamine, 4,4'-diaminodiphenylpropane, 3,3'-diaminodiphenylpropane, 4,4'-diaminodiphenylethane, 3,3'-diaminodiphenylethane, 4,4'-diaminodiphenylmethane, 3,3'-diaminodiphenylmethane, 4,4'-diaminodiphenyl sulfide, 3,3'-diaminodiphenyl sulfide, 4,4'-diaminodiphenylsulfone, 3,3'-diaminodiphenylsulfone, 4,4'-diaminodiphenyl ether, 3,3'-diaminodiphenyl ether, benzidine, 3,3'-diaminobiphenyl, 3,3'-dimethyl-4,4'-diaminobiphenyl, 3,3'-dimethoxybenzidine, 4,4"-diamino-p-terphenyl, 3,3"-diamino-p-terphenyl, bis(p-aminocyclohexyl)methane, bis(p-β-amino-t-butylphenyl) ether, p-bis(2-methyl-4-aminopentyl)benzene, p-bis(1,1-dimethyl-5-aminopentyl)benzene, 1,5-diaminonaphthalene, 2,6-diaminonaphthalene, 2,4-bis(β-amino-t-butyl)toluene, 2,4-diaminotoluene, m-xylene-2,5-diamine, p-xylene-2,5-diamine, m-xylylenediamine, p-xylylenediamine, 2,6-diaminopyridine, 2,5-diaminopyridine, 2,5-diamino-1,3,4-oxadiazole, 1,4-diaminocyclohexane, piperazine, methylenediamine, ethylenediamine, propylenediamine, 2,2-dimethylpropylenediamine, tetramethylenediamine, pentamethylenediamine, hexamethylenediamine, 2,5-dimethylhexamethylenediamine, 3-methoxyhexamethylenediamine, heptamethylenediamine, 2,5-dimethylheptamethylenediamine, 3-methylheptamethylenediamine, 4,4-dimethylheptamethylenediamine, octamethylenediamine, nonamethylenediamine, 5-methylnonamethylenediamine, 2,5-dimethylnonamethylenediamine, decamethylenediamine, 1,10-diamino-1,10-dimethyldecane, 2,11-diaminododecane, 1,12-diaminooctadecane, 2,12-diaminooctadecane, 2,17-diaminoeicosane, diaminosiloxane, 2,6-diamino-4-carboxylic benzene, 3,3'-diamino-4,4'-dicarboxylic benzidine, 2,2-bis[4-(4-aminophenoxy)]propane, 1,3-bis[(3-aminophenoxy)phenyl]benzene, bis[4-(4-aminophenoxy)phenyl]sulfone, 4,4'-bis(4-aminophenoxy)biphenyl, 2,2-bis[4-(4-aminophenoxy)phenyl]tetrafluoropropane and the like. The diamine is not limited to these examples. Moreover, diaminosiloxanes represented by the formula (2) can be used:

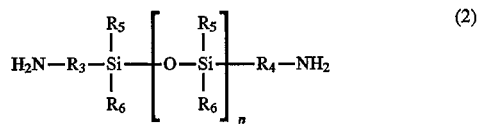

wherein $R_3$ and $R_4$ may be the same as or different from each other and each represents a divalent aliphatic group having 1 to 5 carbon atoms or a divalent aromatic group having 6 or more carbon atoms; $R_5$ and $R_6$ may be the same as or different from each other and each represents a monovalent aliphatic or aromatic group; and n is an integer of 1 to 100. The above diamines may be used alone or in admixture of two or more.

The aprotic polar solvent used in this invention includes, for example, γ-butyrolactone, N,N-dimethylformamide, N,N-dimethylacetamide, N,N-diethylformamide, N,N-diethylacetamide, N,N-dimethylmethoxyacetamide, dimethyl sulfoxide, hexamethylphosphonamide, N-methyl-2-pyrrolidone, pyridine, dimethylsulfone, tetramethylenesulfone, dimethyltetramethylenesulfone, methylformamide, N-acetyl-2-pyrrolidone, diethylene glycol diethyl ether, diethylene glycol dimethyl ether, 1,3-dimethyl-2-imidazolidone, dioxane, tetrahydrofuran, cyclohexanone, and these may be used alone or in admixture of two or more. Non-solvents such as xylene, toluene, cyclohexane and the like may be used in admixture with the above aprotic polar solvents.

In this invention, the reaction temperature is 0° to 50° C., preferably 20° to 30° C. When the temperature is lower than 0° C., the reactivity is low and hence the reaction requires a very long period of time. This is not desirable. When the temperature is higher than 50° C., polymerization of acryl or methacryl group and midization proceed to form a gel. This is not desirable.

The photosensitive resin product obtained according to this invention is usually dropped into a poor solvent such as water, methanol, ethanol, isopropanol or the like for the purpose of purification to precipitate the product and the precipitated product is collected by filtration, dried and then dissolved again in an aprotic polar solvent or the like, and the resulting solution is used. The poor solvent is preferably a solvent in which 1-hydroxy-1,2,3-benzotriazole can be dissolved, and methanol, ethanol and the like are preferred. As the solvent for the dissolution, in addition to the above-mentioned aprotic polar solvents, there can be used carbon-carbon double bond-containing amide compounds and the like. The carbon-carbon double bond-containing amide compound includes, for example, N-methylacrylamide, N-ethylacrylamide, N-methylmethacrylamide, N-ethylmethacrylamide, N,N-dimethylacrylamide, N,N-diethylacrylamide, N-acryloylpiperidine, N-acryloylmorpholine, N,N-dimethylmethacrylamide, N,N-diethylmethacrylamide, N,N-dimethylaminoethylmethacrylamide and the like. However, the above amide compound is not limited to these examples.

Moreover, when the photosensitive resin obtained by this invention is used, a photopolymerization initiator is preferably added thereto for the purpose of enhancing the sensitivity.

As the photopolymerization initiator, the following compounds which are applied to general UV curing resins can be used: Michiler's ketone, benzil, benzoin ethyl ether, benzoin isobutyl ether, benzoin isopropyl ether, benzophenone, benzoylbenzoic acid, methyl benzoylbenzoate, 4-benzoyl-4'-methyldiphenyl sulfide, benzyl dimethyl ketal, 2-n-butoxyethyl-4-dimethylaminobenzoate, 2-chlorothioxanthone, 2,4-diethylthioxanthone, 2,4-diisopropylthioxanthone, 2-dimethylaminoethyl benzoate, ethyl p-dimethylaminobenzoate, isoamyl p-dimethylaminobenzoate, 3,3'-dimethyl-4-methoxybenzophenone, 2,4-diethylthioxanthone, 1-(4-dodecylphenyl)-2-hydroxy-2-methylpropan-1-one, 1-hydroxycyclohexyl phenyl ketone, 2-hydroxy-2-methyl-1-phenylpropan-1-one, 1-(4-isopropylphenyl)-2-hydroxy-2-methylpropan-1-one, isopropylthioxanthone, methylbenzoyl formate, 2-methyl-1-[4-(methylthio)phenyl]-2-morpholinopropanone-1, N-phenylglycine, 1-phenyl-1',2-propandione-2-(O-ethoxycarbonyl)oxime, tetra(t-butylperoxycarbonyl)benzophenone and the like. The photopolymerization initiator is not limited to the above examples. Incidentally, these may be used alone or in admixture of two or more.

For the purpose of further enhancing the sensitivity of the photosensitive resin, a photopolymerizable monomer having a carbon-carbon double bond can be added to the resin. Specific examples of the photopolymerizable monomer include trimethylolpropane triacrylate or trimethacrylate, pentaerythritol triacrylate or trimethacrylate, dipentaerythritol hexacrylate or hexamethacrylate, 1,6-hexanediol diacrylate or dimethacrylate, neopentyl glycol diacrylate or dimethacrylate, ethylene glycol diacrylate or dimethacrylate, diethylene glycol diacrylate or dimethacrylate, tetraethylene glycol diacrylate or dimethacrylate, polyethylene glycol diacrylate or dimethacrylate, 2-hydroxyethyl acrylate or methacrylate, isobornyl acrylate or methacrylate, N-methylolacrylamide, N-methylolmethacrylamide, N,N-dimethylacrylamide and N,N-dimethylmethacrylamide.

To the negative type photosensitive resin composition in which the photosensitive resin of this invention is used, may be added an adhesion promoter, a polymerization inhibitor, a leveling agent and other various fillers.

The negative type photosensitive resin composition in which the photosensitive resin of this invention is used can be used in the following manner. The composition is coated on a suitable support, for example, a silicon wafer, ceramic, aluminum substrate or the like. The coating is effected by spin coating using a spinner, spray coating using a spray coater, immersion, printing, roll coating or the like. Subsequently, the resulting assembly is pre-baked at a low temperature of 60° to 80° C., dried and then irradiated with an actinic radiation so that the desired pattern is formed. As the actinic radiation, there can be used X-rays, electron beams, ultraviolet rays, visible lights and the like, and those having a wavelength of 200 to 500 nm are preferred. In particular, G line and I line rays which are used in the production of semiconductors are preferred.

Subsequently, the unirradiated portions are dissolved in a developing solution to be removed, whereby a negative relief pattern is obtained. As the developing solution, N-methyl-2-pyrrolidone, N,N-dimethylacetamide, N,N-dimethylformamide, γ-butyrolactone, cyclopentane and the like are used alone or in admixture of two or more, or alternatively, in admixture with a poor solvent such as xylene, methanol, isopropanol, water, an aqueous alkaline solution or the like. The developing can be effected by a method such as spraying, puddling, immersion, application of ultrasonic wave.

Subsequently, the relief pattern formed by the development is rinsed. As the rinsing solution, there is used methanol, xylene, ethanol, isopropanol, butyl acetate, water or the like. Thereafter, the rinsed relief pattern is heat-treated to form imide rings, by which a final pattern rich in heat resistance is obtained.

The photosensitive resin composition comprising the photosensitive resin of this invention is useful not only in semiconductor uses but also as a interlaminar insulation film of multilayer circuit, a cover coat of a flexible copper-clad laminate, a solder resist film, a crystal liquid orientation film or the like.

DESCRIPTION OF THE PREFERRED EMBODIMENTS

Examples are shown below to specifically explain this invention.

EXAMPLE 1

In N-methyl-2-pyrrolidone was suspended 322.2 (1.0 mole) g of 3,3',4,4'-benzophenonetetracarboxylic dianhydride, 228.3 g (1.0 mole) of glycerol dimethacrylate and 32.0 g (1.0 mole) of methanol, and then, 166.1 g (2.1 moles) of pyridine was added to the suspension, after which the suspension was subjected to reaction at 25° C. for ten hours.

Subsequently, 270.2 g (2.0 moles) of 1-hydroxy-1,2,3-benzotriazole was added to the reaction mixture and completely dissolved in the latter in the course of one hour. Thereafter, while the reaction system was kept at 10° C. or lower 412.6 g (2.0 moles) of dicyclohexylcarbodiimide dissolved in 400 g of N-methyl-2-pyrrolidone was dropwise added to the reaction system over about 20 minutes, after which the resulting mixture was subjected to reaction at 25° C. for three hours. The reaction mixture was filtered to recover dicyclohexylurea which was then washed and dried. The weight of the thus obtained dicyclohexylurea was 448.6 g and the recovery was 100%.

The reaction mixture was subjected to measurement of infrared spectrum by the NaCl method to confirm an absorption peak of —COON linkage at 1,800 cm$^{-1}$. Moreover, it was confirmed that no absorption peak due to dicyclohexylcarbodiimide was present. To the reaction mixture obtained separately in quite the same manner was added 200.2 g (1.0 mole) of 4,4'-diaminodiphenyl ether, and the resulting mixture was subjected to reaction at 25° C. for five hours. Dicyclohexylurea was removed by filtration and the remaining reaction mixture was reprecipitated from methanol and a polymeric solid was collected by filtration, washed with ethanol and thereafter dried under reduced pressure for 48 hours. The molecular weight of the polymeric solid was measured by a gel permeation chromatography (GPC) to confirm that it was so high that the number average molecular weight was 32,000 and the weight average molecular weight was 55,000.

In addition, 100 g of the polymer obtained was dissolved in 200 g of N-methyl-2-pyrrolidone, and to the solution were added 0.1 g of methyl ether hydroquinone as a polymerization inhibitor, 10 g of Michiler's ketone ($\lambda_{max}$ 365 nm) as a photopolymerization initiator, 5 g of trimethoxysilylpropyl methacrylate as a silane coupling agent and 10 g of diethylene glycol dimethacrylate as an acrylic monomer, and they were dissolved in the solution at room temperature.

The photosensitive resin composition obtained was coated on a silicon wafer by a spinner and dried by means of a drier at 70° C. for one hour to obtain a film. On this film was put a resolution-measuring mask (TOPPAN test chart No. 1) manufactured by TOPPAN PRINTING CO., LTD. and the resulting assembly was irradiated through the mask with 1,000 mJ/cm$^2$ of ultraviolet rays and then developed with a developing solution consisting of 50% by weight of N-methyl-2-pyrrolidone and 50% by weight of xylene upon which a pattern having a resolution of 15 μm was formed.

Moreover, this photosensitive resin composition was coated on a silicon wafer, prebaked and then cured at the final temperature of 350° C., after which the cured film was peeled with a 2% aqueous hydrofluoric acid solution to obtain a film. The tensile strength of this film was 15.5 kg/mm$^2$ which was a sufficient strength for practical use.

EXAMPLE 2

The same procedure as in Example 1 was repeated, except that 130.1 g (1.0 mole) of 2-hydroxyethyl methacrylate was substituted for the glycerol dimethacrylate, to obtain a high molecular weight polymer having a number average molecular weight of 28,000 and a weight average molecular weight of 52,000. To this polymer were added the same photopolymerization initiator, polymerization inhibitor, silane coupling agent and acrylic monomer as in Example 1, and the photosensitive resin composition obtained was subjected to evaluation of patterning to confirm that a pattern having a resolution of 25 μm was formed.

Incidentally, a cured film obtained from this composition had a tensile strength of 12.8 kg/mm$^2$ which was a sufficient strength for practical use.

EXAMPLE 3

The same procedure as in Example 1 was repeated, except that 228.3 g (1.0 mole) of glycerol dimethacrylate was substituted for the methanol, to obtain a high molecular weight polymer having a number average molecular weight of 32,000 and a weight average molecular weight of 75,000. To this polymer were added the same photopolymerization initiator, polymerization inhibitor, silane coupling agent and acrylic monomer as in Example 1, and the photosensitive resin composition obtained was subjected to evaluation of patterning to confirm that a pattern having a resolution of 25 μm was formed.

Incidentally, the cured film obtained from this composition had a tensile strength of 12.4 kg/mm$^2$ which was a sufficient strength for practical use.

EXAMPLE 4

The same procedure as in Example 1 was repeated, except that the temperature at which 4,4'-diaminodiphenyl ether was subjected to reaction was changed from 25° C. to 40° C., to obtain a high molecular weight polymer having a number average molecular weight of 38,000 and a weight average molecular weight of 66,000. To this polymer were added the same photopolymerization initiator, polymerization inhibitor, silane coupling agent and acrylic monomer as in Example 1 and the photosensitive resin composition obtained was subjected to evaluation of patterning to confirm that a pattern having a resolution of 20 μm was formed.

Incidentally, the cured film obtained from this composition had a tensile strength of 14.8 kg/mm$^2$ which was a sufficient strength for practical use.

EXAMPLE 5

The same procedure as in Example 1 was repeated, except that the temperature at which 4,4'-diaminodiphenyl ether was subjected to reaction was changed from 25° C. to 10° C., to obtain a high molecular weight polymer having a number average molecular weight of 32,000 and a weight average molecular weight of 54,000. To this polymer were added the same photopolymerization initiator, polymerization inhibitor, silane coupling agent and acrylic monomer as in Example 1, and the photosensitive resin composition obtained was subjected to evaluation of patterning to confirm that a pattern having a resolution of 21 μm was formed.

Incidentally, a cured film obtained from this composition had a tensile strength of 14.9 kg/mm$^2$ which was a sufficient strength for practical use.

Comparative Example 1

In N-methyl-2-pyrrolidone were dissolved 322.2 g (1.0 mole) of 3,3',4,4'-benzophenonetetracarboxylic dianhydride, 228.3 g (1.0 mole) of glycerol dimethacrylate and 32.0 g (1.0 mole) of methanol, and then 166.1 g (2.1 moles) of pyridine was added to the solution, after which the solution was subjected to reaction at room temperature for ten hours. Thereafter, while the reaction system was kept at 10° C. or lower 412.6 g (2.0 moles) of dicyclohexylcarbodiimide dissolved in 400 g of N-methyl-2-pyrrolidone was dropwise added thereto over about 20 minutes. IR spectrum was measured by the NaCl method to confirm that no absorption peak was present at 1,800 cm$^{-1}$ and no absorption of —COON was confirmed. Subsequently, 200.2 g (1.0 mole) of 4,4'-diaminodiphenyl ether was added to the reaction mixture and the resulting mixture was subjected to reaction at 25° C. for five hours.

The same subsequent treatment as in Example 1 was carried out to obtain a low molecular weight polymer having a number average molecular weight of 8,000 and a weight average molecular weight of 15,000.

Subsequently, to this polymer were added the same photopolymerization initiator, polymerization inhibitor, silane coupling agent and acrylic monomer as in Example 1, and the resulting mixture was subjected to evaluation of patterning to confirm that a pattern having a resolution of 18 μm was formed. However, the tensile strength of the film was 7.5 kg/mm$^2$ which was insufficient for practical use.

Comparative Example 2

The same procedure as in Example 1 was repeated, except that 230.2 g (2.0 moles) of N-hydroxysuccinimide was substituted for the 1-hydroxy-1,2,3-benzotriazole, to obtain a resin, and this resin was treated in the same manner as in Comparative Example 1, to obtain a low molecular weight polymer having a number average molecular weight of 12,000 and a weight average molecular weight of 25,000. To this polymer were added the same photopolymerization initiator, polymerization inhibitor, silane coupling agent and acrylic monomer as in Example 1 and the resulting mixture was subjected to evaluation of patterning to confirm that a pattern having a resolution of 21 μm was formed.

However, a cured film obtained therefrom had a tensile strength of 8.5 kg/mm² which was insufficient for practical use.

Comparative Example 3

The same procedure as in Comparative Example 1 was repeated, except that the temperature at which 4,4'-diaminodiphenyl ether was subjected to reaction was changed from 25° C. to 60° C. After the lapse of two hours, the reaction mixture was solidified and the subsequent operation was impossible.

Comparative Example 4

The same procedure as in Comparative Example 1 was repeated, except that the temperature at which 4,4'-diaminodiphenyl ether was subjected to reaction was changed from 25° C. to −10° C., to obtain a low molecular weight polymer having a number average molecular weight of 6,000 and a weight average molecular weight of 8,000. To this polymer were added the same photopolymerization initiator, polymerization inhibitor, silane coupling agent and acrylic monomer as in Example 1, and the resulting composition was subjected to evaluation of patterning. However, no uniform film was obtained on a silicon wafer when the composition was applied to the silicon wafer, and the evaluation of patterning was impossible.

As is clear from the above Examples and Comparative Examples, only according to this invention, a high molecular weight photosensitive resin having a high sensitivity and excellent cured film characteristics can be easily produced.

What is claimed is:

1. A process for producing a photosensitive resin, which comprises reacting a diamine with a tetracarboxylic acid tetraester represented by the formula (1) at a temperature of 0° to 50° C. in an aprotic polar solvent:

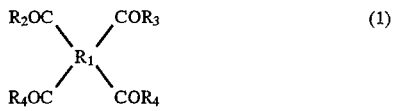

wherein $R_1$ is a tetravalent organic group; $R_2$ is a group represented by the formula:

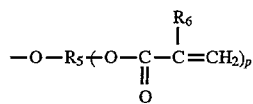

in which $R_5$ is a divalent to hexavalent organic group, $R_6$ is H or $CH_3$ and p is an integer of 1 to 5; $R_3$ is a group represented by $-OCH_3$, $-OC_2H_5$, $-OC_3H_7$ or the formula:

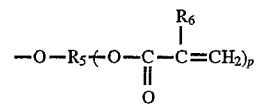

and $R_4$ is a group represented by the formula:

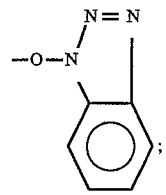

and wherein the tetracarboxylic acid tetraester represented by the formula (1) is obtained by subjecting to addition reaction a tetracarboxylic dianhydride, an alcohol compound represented by the formula $R_2H$ and an alcohol compound represented by the formula $R_3H$ and thereafter subjecting the resulting addition reaction product to dehydration-condensation with 1-hydroxy-1,2,3,7 benzotriazole using a carbodiimide compound as a condensation agent.

2. The process according to claim 1, wherein $R_1$ is an aromatic group, its derivative or a combination of an aromatic group and its derivative.

3. The process according to claim 1, wherein the tetracarboxylic dianhydride is an aromatic tetracarboxylic dianhydride, its derivative or a combination of an aromatic tetracarboxylic dianhydride and its derivative.

4. The process according to claim 1, wherein p is an integer of 1 or 2.

5. The process according to claim 1, wherein the alcohol compound represented by the formula $R_2H$ has 1 or 2 acryl or methacryl groups.

6. The process according to claim 1, wherein each of the alcohol compound represented by the formula $R_2H$ and the alcohol compound represented by the formula $R_3H$ has 1 or 2 acryl or methacryl groups.

7. The process according to claim 1, wherein the diamine is an aromatic diamine, its derivative or a combination of an aromatic diamine and its derivative.

8. The process according to claim 1, wherein the reaction temperature is 20° to 30° C.

* * * * *